United States Patent [19]

Mauz et al.

[11] 4,022,819

[45] May 10, 1977

[54] PROCESS FOR PREPARING CONDENSATION PRODUCTS OF PHENOLS AND ACETOACETIC ACID ESTERS

[75] Inventors: Otto Mauz, Liederbach, Taunus; Norbert Mayer, Augsburg; Günther Nowy, Gersthofen, all of Germany

[73] Assignee: Hoechst Aktiengesellschaft, Frankfurt am Main, Germany

[22] Filed: Dec. 22, 1975

[21] Appl. No.: 643,345

[30] Foreign Application Priority Data

Dec. 27, 1974 Germany .......................... 2461608

[52] U.S. Cl. .......................................... 260/473 S
[51] Int. Cl.² ........................................ C07C 69/76
[58] Field of Search ................................ 260/473 S

[56] References Cited

FOREIGN PATENTS OR APPLICATIONS 1,953,332 5/1971 Germany .......................... 260/473 S
1,953,333 5/1971 Germany .......................... 260/473 S

*Primary Examiner*—Jane S. Myers
*Attorney, Agent, or Firm*—Connolly and Hutz

[57] ABSTRACT

When replacing the low molecular mercaptan used as a catalyst in the known process for preparing condensation products of phenols and acetoacetic acid esters by an n-alkyl mercaptan having of from 8 to 20 carbon atoms, the yield is improved and the reaction time reduced, while the working up of the reaction batch is simultaneously improved.

1 Claim, No Drawings

PROCESS FOR PREPARING CONDENSATION PRODUCTS OF PHENOLS AND ACETOACETIC ACID ESTERS

A process for condensing phenols with esters of acetoacetic acid has been described, wherein the reaction is carried out in the presence of gaseous hydrogen chloride and with the addition of an aliphatic mercaptan as catalyst at a temperature in the range of from $-10°$ to $+15°$ C. Preferred catalysts are low molecular mercaptans such, for example, as methyl and especially ethyl mercaptan used in a quantity of from 0.05 to 0.5% by weight, calculated on acetoacetic acid ester (cf. German Offenlengungsschriften Nos. 1,953,332 and 1,953,333).

This method, however, has various disadvantages. It requires long condensation times (24 hours), while the yields obtained are only moderate. A considerable technical expenditure moreover is required in order to enable using the easily volatile and highly toxic alkyl mercaptans of low molecular weight without risk and treating the reaction mixtures containing mercaptans while fulfilling the requirements concerning the protection of labour and environment.

It has now been found that the aforesaid disadvantages and difficulties can be avoided to a high extent by using instead of the mercaptans of low molecular weight greater quantities of long chain n-alkyl mercaptans as catalysts.

The present invention consequently provides a process for preparing a condensation product of a phenol of formula I and an acetoacetic acid ester of formula II

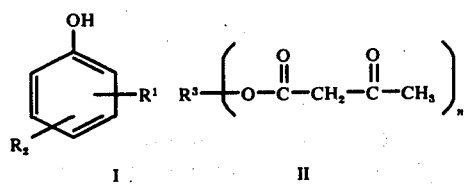

I.      II wherein $R^1$ and $R^2$ are hydrogen atoms or identical or different alkyl radicals having of from 1 to 4 carbon atoms and $R^3$ is a saturated straight chain or branched aliphatic, aromatic, araliphatic or cycoliphatic hydrocarbon radical having of from 1 to 12 carbon atoms and n is an integer of from 1 to 4, in the presence of gaseous hydrogen chloride at a temperature of from $-10°$ to $+15°$ C, which comprises performing the condensation in the presence of from 5 to 30% by weight, calculated on the acetoacetic acid ester used, of an n-alkyl mercaptan having of from 8 to 20 carbon atoms.

It was unexpected that even larger quantities of the long chain n-alkyl mercaptans being undoubtedly substantially less active as compared to alkyl mercaptans of low molecular weight, might still be of technical interest for the intended use, as the diffusion velocity of the first ones decreases with an increasing molecular weight and, consequently, considerably longer condensation times, had to be taken into account. It is therefore surprising that the condensation can be carried out in a briefer, while the yield remains the same or generally is even improved. It is furthermore surprising that long chain mercaptans as well as short chain mercaptans having a branched carbon chain are not at all efficient.

It is moreover advantageous, as compared to the method operating in the presence of alkyl mercaptans of low molecular weight that the long chain n-alkyl mercaptans are less toxic and less odorous than, for example, ethyl mercaptan having a boiling point of 35° C and a MAC value, which is not allowed to exceed 0.5 ppm. The low volatility of the mercaptans of high molecular weight moreover has the following technological advantages for the working up of the batches: A mercaptan may be chosen having a boiling point approximately coinciding with that of the phenol used for condensation in an excess so that the mercaptan may be distilled off from the batch with the excess of phenol when the reaction is terminated and the distillate obtained may be reused for the next batch. Thus the economy of the process can be substantially improved, whereas such a simple working up is not possible when using mercaptans of low molecular weight. In the latter method the mercaptan is withdrawn together with hydrogen chloride and the reaction liquor and cannot be reused with an admissible technical expenditure. Moreover it cannot be avoided that the hydrochloric acid obtainable by combination of the gaseous hydrogen chloride with water has a strong smell of mercaptan and that, consequently, further complicated methods for elimination of this odor are required even if the hydrochloric acid is not intended to be further used, but only neutralized and passed into the waste water. It is moreover advantageous that the long chain mercaptans are scarcely volatile during the condensation performed in a hydrogen chloride current in contrast to the method using ethyl mercaptan, so that the passing speed of hydrogen chloride has no influence on the yield of condensation product.

Suitable starting compounds for the condensation especially are hydroxyaromatic compounds unsubstituted in 4 position of the formula

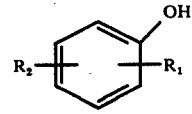

wherein $R_1$ and $R_2$ are hydrogen atoms as well as identical or different alkyl radicals having of from 1 to 4 carbon atoms. There may be mentioned, by way of example, phenol, o-cresol, 2-tertiary-butyl phenol, 2-isopropyl phenol, 2-methyl-6-tertiary-butyl phenol and 2,6-diisopropyl phenol.

Suitable acetoacetic acid esters contain as alcohol component aliphatic, araliphatic, cycloaliphatic or aromatic mono- or polyalcohols, preferably, dialcohols, such as, for example, as methanol, ethanol, propanol, isopropanol, hexanols, dodecanol, ethylene glycol, propanediol-(1,2), propanediol-(1,3), butanediol-(1,4), hexanediol-(1,6), decanediol-(1,10), dodecanediol-(1,12), 2,2-dimethyl propanediol-(1,3), trimethylol propane, glycerin, pentaerythrite, chinite, 1,4-dimethylol cyclohexane, 1,1,4,4-tetramethylol cyclohexane, hydroquinone, resorcinol and dihydroxynaphthalene.

The acetoacetic acid esters may be represented by the general formula

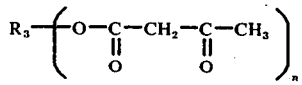

wherein $R_3$ is a saturated straight chain or branched aliphatic, aromatic, araliphatic or cycloaliphatic hydrocarbon radical having of from 1 to 12 carbon atoms and $n$ is an integer of from 1 to 4.

The n-alkyl mercaptans to be used according to the invention in an amount of from 5 to 30, preferably of from 20 to 25% by weight, calculated on acetoacetic acid ester, have of from 8 to 20, preferably of from 8 to 14 carbon atoms. There may be mentioned, by way of example, n-octyl-mercaptan, n-decyl mercaptan, n-dodecyl mercaptan, n-hexadecyl mercaptan, and n-octadecyl mercaptan.

Condensing is effected in the following manner: Acetoacetic acid ester, an excess of phenol and the mercaptan are given into a stirring vessel and dry hydrogen chloride is added while cooling a temperature of from about −10° to +15° C. Condensing is terminated after about 10 to 24, preferably about 12 to 16 hours, which can be seen by the fact that an exothermal heat development can no longer be observed.

For facilitating stirring a polar solvent, such, for example, as anisol or phenetol may be used for dilution. This is especially recommended at the end of the reaction.

When the condensation reaction is terminated, firstly dissolved hydrogen chloride and then the formed reaction liquor are withdrawn by heating them to about 100° C and by applying a vacuum. Then the excess of phenol and the mercaptan and a possibly used solvent are distilled off in vacuo and the remaining distillation residue is recrystallized from a suitable solvent, for example, toluene.

The condensation products obtained according to the invention are suitable inter alia for stabilizing plastic compositions.

The following examples illustrate the invention:

EXAMPLES 1 to 5:

These examples demonstrate the dependence of the yield on the quantity of present mercaptan (The quantity of mercaptan of 1.5% by weight approximately corresponds to the molar mercaptan concentration in the batch obtained when using 0.5% by weight of ethyl mercaptan).

In a 1 liter three-necked flask provided with a stirrer, a gas distribution tube and a gas outlet pipe there were given
  300 g (2.0 moles) of o-tertiary-butyl phenol
  57.5 g (0.25 mole) of acetoacetic acid glycol ester and varying quantities of n-dodecyl mercaptan (of from 1.5 to 24% by weight calculated on acetoacetic acid glycol ester).

whereupon dry HCl gas was introduced through the batch kept at a temperature of from 5° to 10° C for a period of 24 hours at a rate of 100 g per hour. Then the dissolved HCl gas and the reaction liquor formed were distilled off subsequently in a water jet vacuum while slowly increasing the bath temperature and finally, at an oil bath temperature of 180° C, the excess of o-tertiary-butyl phenol (boiling point$_{7 \, mm}$ 110° C) as well as the dodecyl mercaptan (boiling point$_{7 \, mm}$ 133° C).

The residue in the flask was dissolved with 700 ml of toluene at elevated temperature and was caused to crystallize by cooling. The product was drained off, recrystallized from 1,000 ml of toluene and dried in vacuo. A condensation product was obtained having a melting point of 134° C.

The following table shows the yields obtained:

| Example No. | ml of Dodecyl Mercaptan | Yield (%) |
|---|---|---|
| 1 | 1 = 0.85 g = 1.5 % by weight * | 58 |
| 2 | 2 = 1.7 g = 3.0 % by weight | 61 |
| 3 | 4 = 3.4 g = 6.0 % by weight | 74 |
| 4 | 8 = 6.8 g = 12.0 % by weight | 76 |
| 5 | 16 = 13.6 g = 24.0 % by weight | 78 |

*calculated on acetoacetic acid ester.

EXAMPLES 6 to 15:

It can be seen from these examples that not only the yields are improved but the reaction time moreover is also considerably reduced when increasing the mercaptan concentration. The examples were carried out as indicated in Example 1, the quantities of n-dodecyl mercaptan and the reaction times, however, being different.

| Ex. No. | Added Quantity of Dodecyl Mercaptan (ml) | Reaction Time (hrs.) | Yield (%) |
|---|---|---|---|
| 6 | 4 | 12 | 62;45 |
| 7 | 4 | 14 | 71 |
| 8 | 4 | 16 | 71 |
| 9 | 8 | 12 | 54 |
| 10 | 8 | 14 | 72 |
| 11 | 8 | 16 | 75 |
| 12 | 16 | 10 | 63 |
| 13 | 16 | 12 | 78 |
| 14 | 16 | 14 | 78 |
| 15 | 16 | 16 | 78 |

EXAMPLES 16 to 21:

The examples show that the yield of condensation product depends on the passing speed of hydrogen chloride when using a long chain alkyl mercaptan. It was operated as in Example 1. The reaction time was 24 hours.

| Ex. No. | Mercaptan and Quantity | g of HCl/Hour introduced | Yield (%) |
|---|---|---|---|
| 16 | 1 ml of ethyl mercaptan | 6 | 54 |
| 17 | 1 ml of ethyl mercaptan | 130 | 52 |
| 18 | 1 ml of ethyl mercaptan | 206 | 43 |
| 19 | 16 ml of dodecyl mercaptan | 6 | 70.5 |
| 20 | 16 ml of dodecyl mercaptan | 130 | 74.0 |
| 21 | 16 ml of dodecyl mercaptan | 206 | 74.5 |

EXAMPLES 22 to 25:

These examples show that mercaptans having a branching of the carbon chain in α-position to the mercapto group are practically inconvenient for the process of the invention owing to the fact that the desired condensation products are obtained with a low yield. As long chain branched mercaptans may only be isolated with difficulty the isomeric butyl mercaptans were used for these examples. The examples were carried out as Example 1. The reaction time was 24 hours, the addition of mercaptan was 1 ml each time.

| Ex. No. | Mercaptan and Quantity | Yield (%) |
|---|---|---|
| 22 | 1 ml of n-butyl mercaptan | 69 |
| 23 | 1 ml of secondary butyl mercaptan | 42 |
| 24 | 1 ml of tertiary butyl mercaptan | 13 |
| 25 | 1 ml of tertiary butyl mercaptan | 9 |

EXAMPLES 26 to 29:

Condensing was carried out under the same conditions as in Example 5, the time of reaction being 16 hours, with the addition of 24% by weight (calculated on acetoacetic acid ester) of n-dodecyl mercaptan:

| Ex. No. | Phenol (2.0 moles) | Ester (0.25 mole) | Yield (%)* |
|---|---|---|---|
| 26 | o-tertiary butyl phenol | acetoacetic acid isopropyl ester | 86 |
| 27 | o-tertiary butyl phenol | acetoacetic acid n-dodecyl ester | 65 |
| 28 | 2,6-dimethyl phenol | acetoacetic acid isopropyl ester | 75 |
| 29 | 0-tertiary butyl phenol | acetoacetic acid pentaerythrite ester | 72 |

*recrystallized, calculated on acetoacetic ester used.

What is claimed is:
1. A process for preparing a condensation product of a phenol of formula I and an acetoacetic acid ester of formula II

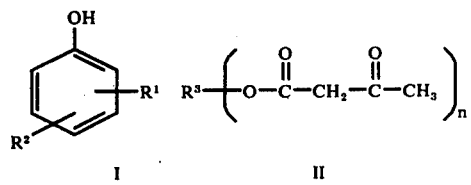

wherein $R^1$ and $-R^2$ are hydrogen atoms or identical or different alkyl radicals having of from 1 to 4 carbon atoms and $R^3$ is a saturated straight chain or branched aliphatic, aromatic, araliphatic or cycloaliphatic hydrocarbon radical having of from 1 to 12 carbon atoms and $n$ is an integer of from 1 to 4, in the presence of gaseous hydrogen chloride at a temperature of from $-10°$ to $+15°$ C, which comprises carrying out the condensation in the presence of from 5 to 30% by weight, calculated on acetoacetic acid ester used, of an n-alkyl mercaptan having of from 8 to 20 carbon atoms.

* * * * *